*US006413499B1*

(12) United States Patent
Clay (10) Patent No.: US 6,413,499 B1
(45) Date of Patent: Jul. 2, 2002

(54) METHODS AND KITS FOR MAXILLARY DENTAL ANESTHESIA BY MEANS OF A NASAL DELIVERABLE ANESTHETIC

(76) Inventor: Bryan M. Clay, 302 Oakmont Trail, Ridgeland, MS (US) 39157

( * ) Notice: Subject to any disclaimer, the term of this patent is extended or adjusted under 35 U.S.C. 154(b) by 0 days.

(21) Appl. No.: 09/567,635

(22) Filed: May 9, 2000

Related U.S. Application Data

(63) Continuation-in-part of application No. 09/528,898, filed on Mar. 20, 2000, now abandoned.
(60) Provisional application No. 60/174,680, filed on Jan. 6, 2000.

(51) Int. Cl.[7] .......................... A61K 7/16; A61K 31/24; A61K 9/127; A61C 5/00
(52) U.S. Cl. ........................ 424/49; 514/535; 514/537; 424/450; 433/215
(58) Field of Search ...................... 128/200.14; 514/817, 514/535, 537; 424/45, 450; D24/152; 433/215

(56) References Cited

U.S. PATENT DOCUMENTS

| 4,562,060 | A | | 12/1985 | Broberg et al. ............... 424/28 |
|---|---|---|---|---|
| 5,134,166 | A | | 7/1992 | Bernstein ...................... 514/627 |
| 5,180,371 | A | | 1/1993 | Spinello ........................ 604/118 |
| 5,366,489 | A | | 11/1994 | Burgio et al. .................. 607/47 |
| 5,368,572 | A | | 11/1994 | Shirota .......................... 604/154 |
| 5,446,070 | A | * | 8/1995 | Mantelle ..................... 514/772.6 |
| 5,496,363 | A | | 3/1996 | Burgio et al. ................ 607/152 |
| 5,534,242 | A | * | 7/1996 | Henry ........................... 424/45 |
| 5,563,153 | A | | 10/1996 | Mueller et al ............... 514/305 |
| 5,571,071 | A | | 11/1996 | Shapiro ........................ 600/187 |
| 5,593,661 | A | | 1/1997 | Henry ........................... 424/45 |
| 5,858,331 | A | * | 1/1999 | Henry ........................... 424/45 |
| 5,942,543 | A | | 8/1999 | Ernst ............................ 514/537 |
| 6,022,337 | A | | 2/2000 | Herbst et al. ................ 604/131 |

OTHER PUBLICATIONS

Tarver et al., *A Comparison of Cocaine vs. Lidocaine with Oxymetazoline for Use in Nasal Procedures*, Otolaryngology—Head and Neck Surgery, vol. 109, No. 4, pp. 653–659 (Oct. 1993).

(List continued on next page.)

*Primary Examiner*—Frederick Krass
*Assistant Examiner*—Donna Jagoe
(74) *Attorney, Agent, or Firm*—Workman, Nydegger & Seeley (57) ABSTRACT

Methods and systems for anesthetizing a portion or all of a patient's maxillary dental arch using a nasal delivered anesthetizing composition. The process generates anesthesia sufficient for facilitation of operative dentistry, endodontics, periodontics or oral surgery for teeth of the maxillary arch. The dental nasal spray process consists of inserting one or more dispensing devices through the patient's nostril and delivering metered dosages of anesthetic solution or gel into the nasal cavity. The process may utilize a single solution which is a mixture of anesthetic agents, vasoconstricting agents and other physiological inert agents or two separate solutions, wherein one solution contains the vasoconstricting agents and the other solution contains the anesthetic agents. Anesthetic diffusion through the thin walls of the nasal cavity allows for the blocking of nerve impulses originating from the maxillary dentition and surrounding tissues. Anesthesia of specific oral regions such as right versus left sides of the dental arch, anterior versus posterior teeth, and soft tissue anesthesia may be controlled through modification of the dosage volume and the selection of right or left nostril insertion and agent delivery.

32 Claims, 7 Drawing Sheets

OTHER PUBLICATIONS

Noorily et al., *Intranasal Anesthetic Effects of Lidocaine and Tetracaine Compound*, Otolaryngol–Head and Neck Surgery, vol. 113, No. 4, pp. 370–374 (Oct. 1995).

Noorily et al., *Cocain, Lidocaine, Tetracaine: Which is Best for Topical Nasal Anesthesia?*, Anesth. Analy., vol. 81, pp. 724–727 (1995).

Greenfield et al., *Evaluation of Anesthetic Agents on Human Mucous Membrane: An Illustration of Experimental Protocol Using Computers*, NYS Dental Journal, pp. 22–28 (Oct. 1996).

Gaskill et al., *Local Anesthesia for Peroral Endoscopy: Using Superior Laryngeal Nerve Block with Topical Application*, Arch. Otalaryny., vol. 84, pp. 654–657 (Dec. 1996).

DiFazio, C.A., *Local Anesthetics: Action, Metabolism, and Toxicity*, Otolaryngologic Clinics of North America, vol. 14, No. 3, pp. 515–519 Aug. 1981.

Cetacaine Product Literature, published by Cetylite Industries, webpage printed Nov. 1999.

Advertisement by Fairfax Dental, Dentistry Today, p. 13 (Dec. 1997).

\* cited by examiner

METHODS AND KITS FOR MAXILLARY DENTAL ANESTHESIA BY MEANS OF A NASAL DELIVERABLE ANESTHETIC

RELATED APPLICATIONS

This application is a continuation-in-part of copending U.S. application Ser. No. 09/528,898, filed Mar. 20, 2000, now abandoned, which claims the benefit of priority to copending U.S. Provisional Application Ser. No. 60/174,680, filed Jan. 6, 2000. For purposes of disclosure, the foregoing applications are incorporated herein by reference.

BACKGROUND OF THE INVENTION

1. The Field of the Invention

The invention disclosed herein is in the field of anesthesia, more particularly the field of dental anesthesia. More particularly, the invention is in the field of nasal deliverable anesthesias that are sprayed or otherwise placed in the nasal cavity in order to numb the nerves associated with pain sensations generated by teeth and surrounding tissue within the maxillary dental arch.

2. The Relevant Technology

Most people fear going to the dentist. They equate visiting the dentist with pain. The most excruciating pain is typically caused by the drilling of cavities, root canal procedures, the pulling of teeth, crown and bridge work, and other procedures which disrupt, damage or otherwise put pressure on the pulp of a tooth and/or the surrounding maxillary bone and gingiva.

Various techniques have been employed to reduce the pain associated with the aforementioned dental procedures. The most common procedure to relieve or reduce dental pain is the application of a local anesthetic into the surrounding gingival tissue adjacent to the tooth. Alternatively, some dentists have found it useful to inject the anesthetic directly into the alveolar bone adjacent to the operative area. In many cases, application of the local anaesthetic by needle injection is itself very painful. The fear of needles is so great in some individuals that the injection can be more traumatic than the dental procedure itself. As between the upper and lower dental arches, most people believe that the pain associated with injecting a local anaesthetic to the upper dental arch is greater than with the lower dental arch.

Another source of fear is the possibility of failure of the anesthesia, which may result from incorrect placement of the anaesthetic. The duration of operative anesthesia may be unexpectedly short due to incorrect placement, the failure providing the correct dosage, or premature destruction of the anesthesia due to inflammation and associated low tissue pH. The proper dosage of anesthesia can vary greatly from one patient to the next, and can vary in the same patient due to biological variation, anxiety, fear, or infection in the area. The fear and anxiety associated with painful injections may actually deter some people from seeking dental work, even badly needed dental work required to relieve immediate pain and to correct serious acute or chronic conditions.

Complications can also occur with local injections. Locally, infections can occur and be transmitted through a contaminated needle. Improper placement of the needle can result in tearing or ripping of local tissue and nerves, as can delivering too large a volume of anesthetic to an area. Blood vessels can be lacerated when making regional blocks which may result in hematoma formation. In view of the foregoing, there has been a long-felt need to find alternatives to needle administered anesthesia.

One attempt at helping patients to overcome their fear of dental injections is the preliminary application of topical anesthetics in the form of gels, liquids, sprays, or patches to the gingival area where it is desired to insert the needle with the local anaesthetic. A topical anesthetic having a liquid or gel consistency and containing lidocaine, tetracaine, and adrenaline or epinephrine is described in U.S. Pat. No. 5,942,543 to Ernst. Another topical anesthetic gel composition, which purportedly aids in wound repair and hemostasis, is described in U.S. Pat. No. 5,563,153 to Mueller et al. The problem with topical anesthesia is at least two-fold: (1) patients still fear the needle and (2) the needle is still very painful once injected beyond the numbed gingival surface. In reality, topical anesthetics are only truly effective in relieving pain associated with superficial procedures such as suturing a laceration. Topical anesthetics do not effectively alleviate dental pain involving a tooth or the surrounding bone.

Yet another attempt at delivering a pain-free injection is disclosed in U.S. Pat. No. 5,180,371 to Spinello, which describes an aspirating hypodermic syringe capable of automatically injecting the dental anesthetic independent of squeezing by the dentists fingers. Spinello claims that the local anesthetic can be delivered even while the needle enters the tissue and then at different flow rates. The problem with the Spinello device is that it still involves an injection by a painful needle and, in view of the varying set flow rates intended to reduce pain, the length of time of the injection process is actually longer than manually performed injections. There is also the additional high cost of the device, both for the dentist and the patient. Attempts at improving the dental anesthetic pump are disclosed in U.S. Pat. No. 6,022,337 to Walter et al. and U.S. Pat. No. 5,368,572 to Shirota.

An attempt to alleviate a patient's fear and anxiety of a needle by eliminating the needle altogether is described in U.S. Pat. Nos. 5,366,489 and 5,496,363 to Burgio. The Burgio patents claim to provide a needleless method for relieving pain by means of electrical impulses applied to local tissues in an attempt to temporarily block nerve sensations. This method is referred to as "transcutaneous electrical nerve stimulation", or "TENS". In practice, the TENS method may actually provide enough blockage of sensation to allow for minor dental procedures, or to facilitate less painful injections for more involved dental procedures. However, this method has failed to save patients from having to endure painful injections when more intrusive and, hence, more painful, dental procedures are involved. Moreover, the TENS method has been associated with unpredictable results and has been generally ignored by the dental market. It is far more costly than simply providing topical anesthetics prior to dental injections.

One of the problems with anesthetizing teeth is the problem of accessing the nerves responsible for dental pain sensations. Because of the location of dental nerves, finding and numbing the nerves responsible for the pain sensation is not a very simple task. The same is not true for internal nasal tissues. Since internal nasal tissues include a large area of very thin mucous membrane tissue, topical anesthetics would be expected to be quite effective in immediately numbing pain for purposes of nasal surgery, such as the removal of polyps. This is in sharp contrast to teeth, which are completely immune to topical anesthetics applied thereto.

Accordingly, other interesting medical developments have been in the field of topical anesthetic sprays and aerosols used to deliver local anesthesia to the area of the larynx and respiratory system. For example, U.S. Pat. No. 5,571,071 to Shapiro discloses an improved laryngoscope blade having an attached anesthetic-containing reservoir for providing an anesthetic spray at one end of the blade. In addition, a fluid delivery means is included for providing anesthetic to other surfaces of the blade. U.S. Pat. No. 5,593,661 to Henry discloses the delivery of a selected dosage of lidocaine in an aerosolized form from a canister. The anesthetic so delivered is said to be useful in delivering anesthesia to a patient's respiratory system, either directly or by way of an airway.

In view of the foregoing, it would be an improvement in the art to provide improved methods and systems for delivering a local anesthetic in connection with painful dental procedures, which was less painful to administer compared to conventional needle delivered anesthetics.

It would be an additional improvement in the art to provide methods and systems for delivering a local anesthetic in connection with painful dental procedures which eliminated the use of needle delivered anesthetics altogether, at least with respect to a portion of a patient's teeth, particularly at least a portion of the patient's upper dental arch, which is the most painful to anesthetize using a needle.

It would be a tremendous improvement in the art if such methods and systems for painlessly delivering a local anesthetic without the use of a needle also provided complete and total anesthetization of at least a portion of a patient's teeth, particularly at least a portion of the patient's upper dental arch, which is the most painful to anesthetize using a needle.

It would be an additional improvement in the art to provide methods and systems for painlessly anesthetizing a patient's teeth without the use of a needle, which further allowed for the painless anesthetization of surrounding gingival tissues.

Such methods and systems for painlessly delivering a local anesthetic without the use of a needle in order to anesthetize at least a portion of patient's teeth and surrounding tissues are disclosed and claimed herein.

SUMMARY AND OBJECTS OF THE INVENTION

The present invention relates to methods and systems for anesthetizing a patient's teeth and surrounding palatal tissues within the maxillary dental arch by means of a nasal deliverable anaesthetic. Such methods and systems eliminate altogether the need for painful needle injected local anesthetics when preparing a patient for dental work on the maxillary, or upper, dental arch. By this means, patients will have less fear and anxiety when visiting a dentist and will experience greatly decreased pain associated with the application of the local anesthetic preparatory to carrying out the actual dental procedure. Moreover, because the nasal delivered anesthesia is total, complete and more easily administered compared to needle injected anesthetics, there is less danger of the anesthetic not taking effect or prematurely losing its anesthetizing effect compared to needle delivered anesthetics. The delivery of the anesthetics through topical absorption in the nasal cavity also eliminates the potential for accidental intervascular administration of anesthetics, as can occur during the administration of local, needle-delivered nerve blocks.

The nasal deliverable anesthetizing composition comprises one or more anesthetizing agents, such as lidocaine, tetracaine, or benzocaine, together with an appropriate liquid or gel carrier. The anesthetic composition may also include one or more vasoconstrictors in order to ensure more rapid uptake of the anesthetizing agent and also to help maintain the anesthetic localized in the desired area. The carrier may include any appropriate liquid or gel which yields an anesthetic composition having a desired rheology, pH, absorbability, and the like. Any other active agent or passive constituent may be added in order to provide any desired benefit to the patient, manufacturer, or person administering the anesthetic.

The nasal deliverable anesthetizing method may be employed through delivery of a single mixture of one or more an anesthetic agents, one or more vasoconstricting agents and associated carriers, or through delivery of multiple solutions. Ideally, the sequence of multiple solution delivery would be delivery of the vasoconstricting composition, followed by delivery of the anesthetic composition. A time period of one to ten minutes between administration of the two components may be beneficial in order to allow for maximum vasoconstriction and opening of the nasal canals prior to administration of the anesthetic composition.

The anesthetic composition may be introduced into a patient's nasal cavity by means of any appropriate delivery system known in the art for delivering a nasal spray or nasal anesthetic. Examples include hand-held spray bottles, single dosage pump sprayers, pressurized aerosol canisters, pneumatically actuated sprayers, syringes or squeeze bottles equipped with tubular extensions, and the like. The delivery systems may be modified to provide for set dosages to be delivered. Atomizers or other means for providing a fine mist or spray are presently preferred, although the anaesthetic composition may certainly be applied as an non-atomized liquid, gel or even a solid, such as a powder. Delivery systems that better control the range or area of application may be better suited in anesthetizing only a portion of the patient's teeth rather than the entire maxillary dental arch.

The inventor, who is an ear, nose and throat specialist by trade, found that, after anesthetizing a patient's nasal cavity using a nasal delivered anesthesia preparatory to nasal procedures, the patient complained of extensive numbing of the upper dental arch, which the patient considered to be an undesirable side effect. Upon further analysis and inquiry, this unintended and undesired side effect of tooth numbing resulted from accidental application and absorption of the anesthetic in the region of the maxillary nerve and the pterygopalatine ganglion, a concentrated bundle of nerves located at the extreme rear upper end of the nasal cavity. The maxillary nerve is where the posterior, middle and anterior superior alveolar nerves collect, which are responsible for initially transmitting pain, temperature and pressure impulses generated by the nerves of the maxillary dentition and surrounding maxillary bone. After the impulses pass through the maxillary nerve and the main trunk of the trigeminal nerve, they are transmitted to the brain for processing and recognition.

The nasal deliverable anesthetizing compositions of the present invention are therefore believed to work by anesthetizing at least a portion of the branches of the maxillary nerve. Depending on the extent of anesthetization of the maxillary nerve and its associated branches, it is possible to numb the pain of part or all of the teeth and surrounding tissues of the maxillary arch. Moreover, introducing the nasal deliverable anesthesia into the left or right nasal cavities affects whether the left or right halves of the maxillary dental arch are anesthetized. This is fortunate, because it so happens that the teeth and surrounding tissue of the maxillary arch are the most painful and difficult parts of the mouth to properly anesthetize. By this means the dentist can more carefully control the location and extent of the anesthesia.

The surrounding facial gingival tissue (that which lies between the teeth and the lips) is not entirely anesthetized by the foregoing procedure, but may be readily and easily anesthetized by any desired means, such as by applying a topical anesthesia or a shallow and less painful injection of a local anesthesia.

The nasal deliverable anesthetic compositions of the present invention are unique in the field of dentistry. They offer the dentist, and more importantly the patient, a convenient and far less traumatizing method for obtaining profound anesthesia of the maxillary dentition, hard palate and soft palate. In particular, they offer complete elimination of patient fear of needle injections, as well as complete elimination of the pain associated with needle injections. The methods and systems of the present invention are far less technique-sensitive compared to needle injections. They eliminate, or at least reduce, the incidence of sharp biohazard wastes associated with used syringe needles. They eliminate the risk of accidental I.V. administration of local anesthetic/vasoconstricting solutions. They are completely effective in anesthetizing teeth with active infections that can render local, needle-delivered anesthetics ineffective due to inflammation and associated low pH. They provide partial or complete anesthesia of the maxillary dental arch without anesthetizing the lips. Finally, by alleviating the pain and fear associated with needle delivered anesthetics, they may encourage more people to seek help from a dentist in correcting health threatening dental maladies.

Accordingly, it is an object of the invention to provide improved methods and systems for delivering a local anesthetic in connection with painful dental procedures, which is less painful to administer compared to conventional needle delivered anesthetics.

It is an additional object and feature of the invention to provide methods and systems for delivering a local anesthetic in connection with painful dental procedures which eliminate the use of needle delivered anesthetics altogether, at least with respect to a portion of a patient's teeth, particularly at least a portion of the patient's maxillary dental arch, which is the most painful to anesthetize using a needle.

It is a further object and feature of the invention to provide methods and systems for painlessly anesthetizing a patient's teeth without the use of a needle, which further allows for the painless anesthetization of surrounding gingival tissues.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

I. Introduction

The present invention relates to methods and systems for applying a local anesthetic to a patient's teeth and surrounding maxillary tissue within the maxillary dental arch without the need for a needle to inject a local anesthetic. Instead, a topical anesthetic is applied in the form of an aerosol spray, gel or powder that is absorbed within the nasal cavity. The topical anesthetic works by being absorbed by the nasal cavity tissue in the vicinity of the nerves responsible for transmitting pain impulses from a person's maxillary dentition and surrounding tissue to the brain. By this means, patients will experience far less, or often even no pain at all, as well as less fear and anxiety, compared with the situation associated with conventional needle-delivered local anesthetics. Moreover, nasal delivery of the anesthesia is more easily administered compared to needle injection, and there is less danger of the anesthetic not taking effect or wearing off prematurely, as is sometimes the case with needle-delivered anesthetics.

Figure 1:
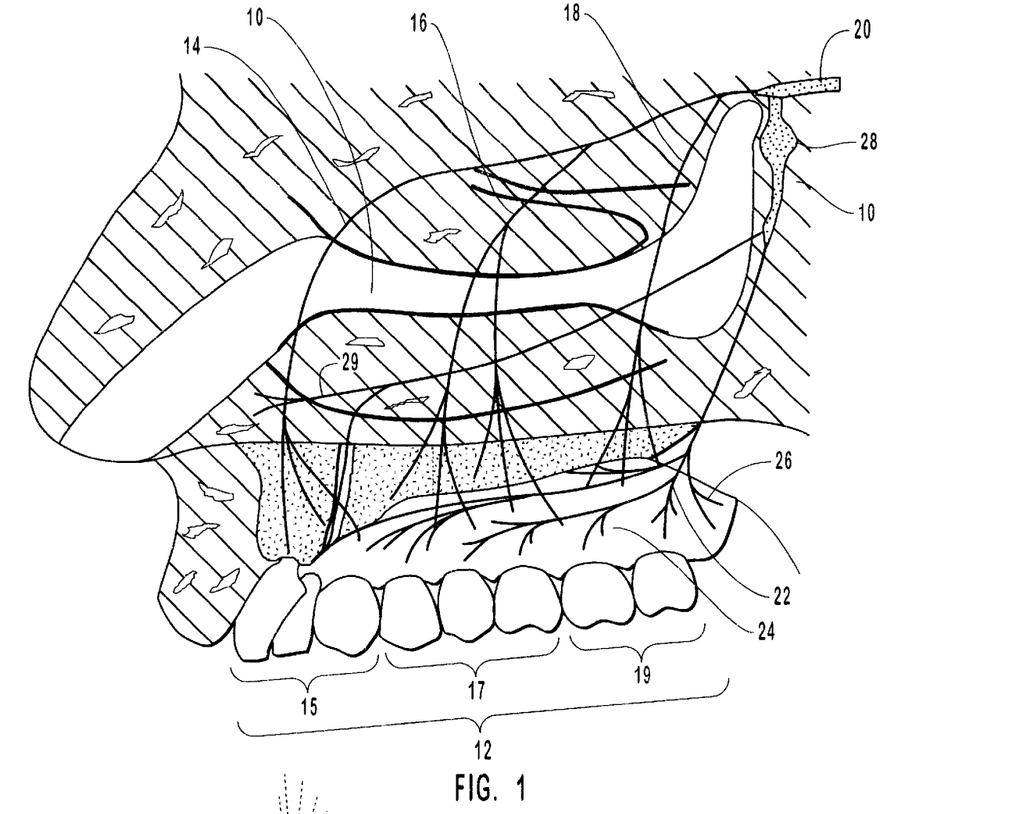
FIG. 1 is a cross-sectional side view of the nasal cavity and dentition, and also certain selected nerves pertaining thereto.

By way of background, FIG. 1 is a cross-sectional side view of a person's nasal cavity 10, one hemisphere of the maxillary dentition 12, and associated nerves. The anterior superior alveolar nerve 14, the middle superior alveolar nerve 16, and the posterior superior alveolar nerve 18 have their nerve endings in the front 15 teeth, middle teeth 17, and rear teeth 19, respectively. They, as well as the "preceding nerves", are the nerves that are primarily responsible for sending pain impulses from the teeth 12 to the brain (not shown). They join together at the maxillary nerve 20 deep within the nasal cavity 10. The maxillary nerve 20 is a major nerve bundle where numerous nerves come together. The term "preceding nerves" includes those nerves upstream from the aforementioned nerves located in a more central neural bundle.

The greater palatine nerve 22 originates in the hard palate 24 and, along with the preceding nerves, is the nerve responsible for transmitting pain impulses from the hard palate 24 to the brain. The lesser palatine nerve 26 originates in the soft palate (not shown) within a person's mouth and, along with the preceding nerves, is the nerve responsible for transmitting pain impulses from the soft palate to the brain. The greater and lesser palatine nerves 22, 26 collect deep within the nasal cavity 10 at the pterygopalatine ganglion 28. The nasopalatine branch 29 of the anterior superior alveolar nerve 14 communicates between the alveolar nerves and the palatine nerves.

Because all of the foregoing nerves are near the surface of the nasal cavity 10, particularly at the rear of the nasal cavity 10, it is possible to apply anesthesia to these nerves by means of an absorbable topical anesthetic applied to wall of the nasal cavity 10.

As it will be discussed hereinbelow, the topical anesthetic may take a variety of forms and is not limited to any particular anesthetic. In addition, the anesthetic can be more easily absorbed when applied in combination or in series with a vasoconstrictor. The vasoconstrictor can be any vasoconstrictor known in the art and may be applied prior to or simultaneously with the application of the anesthetic. In addition, the vasoconstrictor aids in inhibiting migration of the anesthetic away from the nerves being treated, and it shrinks nasal tissues therefore allowing for greater and deeper anesthetic penetration into the nasal cavity. Both the anesthetic and vasoconstrictor are advantageously dissolved or dispersed within an appropriate carrier, such as an aqueous liquid or gel carrier, in order to control their dosage and assist in their absorption by the nasal tissue.

The nasal deliverable anesthetizing composition can be applied using any means known in the art. In a preferred embodiment, the anesthetic and vasoconstrictor are applied using a delivery device capable of providing an absorbable spray or powder of the anesthetic agent. The anesthetizing agent, vasoconstrictor and delivery device may advantageously be sold as a kit for ease of use by the dentist.

The process of anesthetizing the maxillary dental arch through the dental nasal spray process represents a significant step forward in dentistry's progression toward a less fearful dental experience for the patient. The dental nasal spray process is unique in its ability to yield profound dental anesthesia to the maxillary dental arch without the use of a needle or a needle-like delivery device. The ability of this process to avoid the dominant dental phobia of injections is of great significance for dentist and patient alike. All facets of the dental sciences would benefit through utilization of the dental nasal spray process. At lower dosing volumes, operative (adult and pediatric) procedures and endodontic procedures would be facilitated. At higher dosing volumes, periodontal and oral surgery procedures would be facilitated due to additional soft tissue anesthesia.

II. Compositions and Constituents

The components of the nasal deliverable anesthetizing compositions within the scope of the invention typically comprise three main classes of substances: topical anesthetics, vasoconstrictors and physiologically inert substances. The topical anesthetic may be utilized alone, or within a mixture of multiple active agents, and is the main agent responsible for numbing the maxillary dentition and surrounding tissue. The function of the vasoconstrictors is to contract nasal tissues to allow for improved penetration and absorption of the anesthetic and to limit systemic migration thereof once absorbed by the desired tissue. Physiologically inert agents may be used in the solution for purposes such as modification of substance wetting, control of mixture viscosity, mixture dilution and control of solution pH.

A. Nasal Deliverable Anesthetizing Agents.

A wide range of anesthetics known in the art may be used within the scope of the invention. Preferred anesthetics, or "anesthetizing agents", include the known local anesthetics rather than general anesthetics that anesthetize the central nervous system. Local anesthetics include, for example, benzocaine, butacaine, tetracaine, lidocaine, dyclonine, pramoxine, dibucaine, and cocaine. The foregoing anesthetics may be delivered to the nasal cavity in any form, such as a liquid solution, a suspension, a gel, or a powder.

In a preferred embodiment, one or more topical anesthetics are delivered to the nasal cavity in the form of an aqueous solution or gel. Because the foregoing anesthetics are not readily soluble in water, they may advantageously be converted into a more soluble form, such as in the form of a salt. For example, the anesthetics may be reacted with an appropriate mineral acid, such as hydrochloric acid or sulfuric acid, in order to yield the salt of the anesthetic. These include, for example, tetracaine hydrochloride, lidocaine hydrochloride, dyclonine hydrochloride, pramoxine hydrochloride, dibucaine hydrochloride, butacaine sulphate, and cocaine hydrochloride.

It should be understood that the foregoing anesthetics are merely exemplary and not limiting. In addition, it is certainly within the scope of the present invention to use analogues or other derivatives of the foregoing so long as they can impart a topical anesthetizing effect. The foregoing topical anesthetics may also be used to directly anesthetize the patient's gingiva, such as by direct application of an anesthetic composition to the gingiva.

The desired concentration of the anesthetic is dependent upon the specific anesthetic being used as well as the desired anesthetizing strength and activity of the anesthetic. In general, the concentration of the anesthetic will be similar to the concentration used for other topical applications known in the art. Accordingly, the anesthetic, when used within an aqueous liquid or gel, will be included in an amount in a range from about 0.1% to about 50% by weight of the composition, more preferably in a range from about 0.5% to about 25% by weight, and most preferably in a range from about 1% to about 10% by weight of the composition.

B. Vasoconstrictors.

Any vasoconstrictor known in the art may be used within the scope of the present invention. Presently preferred vasoconstrictors include, but are not limited to, oxymetazoline, phenylephrine, naphazoline, propylhexadrine, levodexoxyephedrine, epinephrine and norepinephrine. The vasoconstrictor may be applied in any desired form, either alone or in combination with one or more anesthetics.

In a preferred embodiment, the vasoconstrictor will be dissolved within an aqueous liquid or gel. As with the anesthetics discussed above, it may be advantageous to convert the foregoing vasoconstrictors into a more water-soluble form, such as a salt. This may be done, for example, by reacting them with an appropriate acid in order to yield, e.g., oxymetazoline hydrochloride, phenylephrine hydrochloride, and naphazoline hydrochloride.

The purpose of applying a vasoconstrictor before, during and/or after applying the anesthetic is at least two-fold. First, the vasoconstrictor shrinks nasal tissue in order to promote penetration of the anesthetic deeper into the nasal cavity. Second, once the anesthetic has been absorbed into a desired area, the vasoconstrictor inhibits systemic migration of the anesthetic. This, in turn, helps to maintain the anesthetizing effect in the desired area. It also increases the length of time the anesthetic is able to anesthetize the desired tissue.

Vasoconstrictors are typically effective at very low concentrations. The desired concentration will be dependent on the particular vasoconstrictor being used and the desired vasoconstricting effect. Accordingly, when used in an aqueous liquid or gel, the vasoconstrictor will preferably be included in an amount in a range from about $10^{-6}\%$ to about 2% by weight of the composition, more preferably in a range from about $10^{-5}\%$ to about 1% by weight, and most preferably in a range from about 0.001% to about 0.5% by weight of the composition.

C. Other Active Agents.

It is certainly within the scope of the invention to include any other active agent within the nasal deliverable anesthetizing compositions according to the present invention. Examples of additional active agents include one or more antihistamines to inhibit nasal drip during and after the dental procedure, antioxidants and other preservatives, and the like. Examples of antihistamines capable of inhibiting nasal drip include, but are not limited to, atropine and azelastine HCl.

D. Carriers.

The anesthetics, vasoconstrictors and other active agents may be advantageously dispersed within an appropriate carrier in order to control the dosage, absorption rate, and other desired properties. In one embodiment, the active agents are dissolved within an aqueous liquid, preferably a physiologically balanced saline solution. The saline solution will typically include buffers known in the art in order to control the pH of the solution so that it is compatible with the nasal cavity. One of ordinary skill in the art will be able to provide an appropriate physiologically balanced saline solution, including a solution having appropriate buffers to control the pH.

In order to enhance their solubility in water and other aqueous carriers, active ingredients that are not water soluble, or only slightly water soluble, are preferably treated to make them more water soluble, as stated above. Making the active agents water soluble has been found to generally enhance the rate of penetration and absorption of the foregoing active agents through nasal membrane tissue. In the alternative, it is certainly within the scope of the invention to provide one or more active ingredients in the form of a suspension of insoluble particulates, an emulsion of immiscible components, or a nonaqueous solution.

In one embodiment it may be desirable to disperse the active agents within an aqueous gel. A "gel" is characterized as having a viscosity such that the composition may adhere to and remain in place when applied to nasal membrane tissue. Any appropriate gelling agent may be mixed with, e.g., water or a physiologically balanced saline solution in order to yield a desired gel carrier. Example of gelling agents include cellulosic ethers, e.g., hydroxyethylcellulose, methylhydroxyethylcellulose, hydroxymethylethylcellulose, carboxymethylcellulose, methylcellulose, ethylcellulose, hydroxyethylpropylcellulose, hydroxy and propylmethylcellulose; polyalkylene oxides, e.g., polyethylene glycol, polypropylene glycol; natural gums, e.g., xanthan gum, talha gum, tragacanth gum, locust bean gum, guar gum, irish moss gum, ghatti gum, furcelleran gum, carrageenan gum, arabic gum, alginic acid gum, agar gum, alginate gum; carboxypolymethylene; and the like. PEMULEN® is a proprietary formulation of B. F. Goodrich that includes a significant quantity of a polyacrylic copolymer that has a slightly hydrophobic end and a strongly hydrophilic end.

There is typically a tradeoff between employing a liquid carrier versus a gel carrier. Whereas the liquid carrier is superior in terms of the rate and extent of penetration and absorption of the active agents, the gel carrier is superior in terms of tissue adhesion and the ability to remain where initially placed. In the case where it is desired for the nasal delivered anesthetic composition to become more completely atomized, a liquid carrier will generally be preferred. Thus, the use of liquid carriers that are readily atomized or sprayed yield compositions that may be suitable for a wider variety of dispensers. Gel carriers that are not easily atomized are generally better suited for dispensers capable of reaching back into the nasal cavity to where it is desired to place the anesthetic composition.

Finally, it is within the scope of the invention to provide other carriers, such as organic solvent carriers. Examples of suitable organic solvents include glycerin, sugar alcohols, polyethylene glycol, polypropylene glycol, and the like. Even dry powder carriers are within the scope of the invention, such as when it is desired to provide a dry, inhalable powder. The powder carrier is preferably inert, will not irritate the nasalis and nasal cavity, and is used mainly to control the concentration, and hence the potency, of the active ingredients. The powder carrier may be any physiologically compatible substance known in the art, such as an inert powder.

III. Means for Delivering the Inventive Compositions

A. Delivery Devices.

It is within the scope of the invention to provide or deliver the anesthetic compositions of the present invention using any known delivery device. Examples of suitable delivery devices include, but are not limited to, squeeze bottles, pump sprayers, syringes, pneumatically pressurized devices, tubular extensions, and the like. These devices will now be described in more detail.

Figure 2:
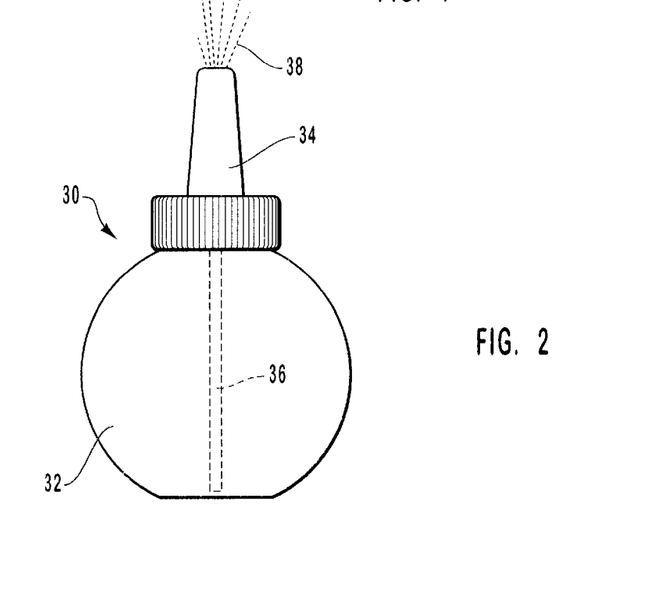
FIG. 2 is a side perspective view of an exemplary spray bottle that may be used to deliver a nasal deliverable anesthetizing composition into a patient's nasal cavity.

FIG. 2 depicts a conventional squeeze bottle used to deliver a nasal spray, such as a saline solution or a decongestant. The squeeze bottle 30 includes a flexible liquid reservoir 32 and a spray nozzle 34. A tube 36 communicates between the reservoir 32 and the nozzle 34 in order to force a liquid 38 out through the nozzle upon squeezing the flexible liquid reservoir 32. The liquid 38 is typically delivered in the form of a fine mist or spray. An air vent (not shown) associated with the tube 36 or nozzle 34 allows for the mixing of air and liquid together upon squeezing the flexible reservoir 32. The squeeze bottle 30 may be a single-use dispenser, or it may be suitable for multiple applications. In order to avoid infection, the squeeze bottle 30 should only be used by a single person, and disposable sterile tips (not shown) may be used to prevent cross-patient contamination.

Figure 3:
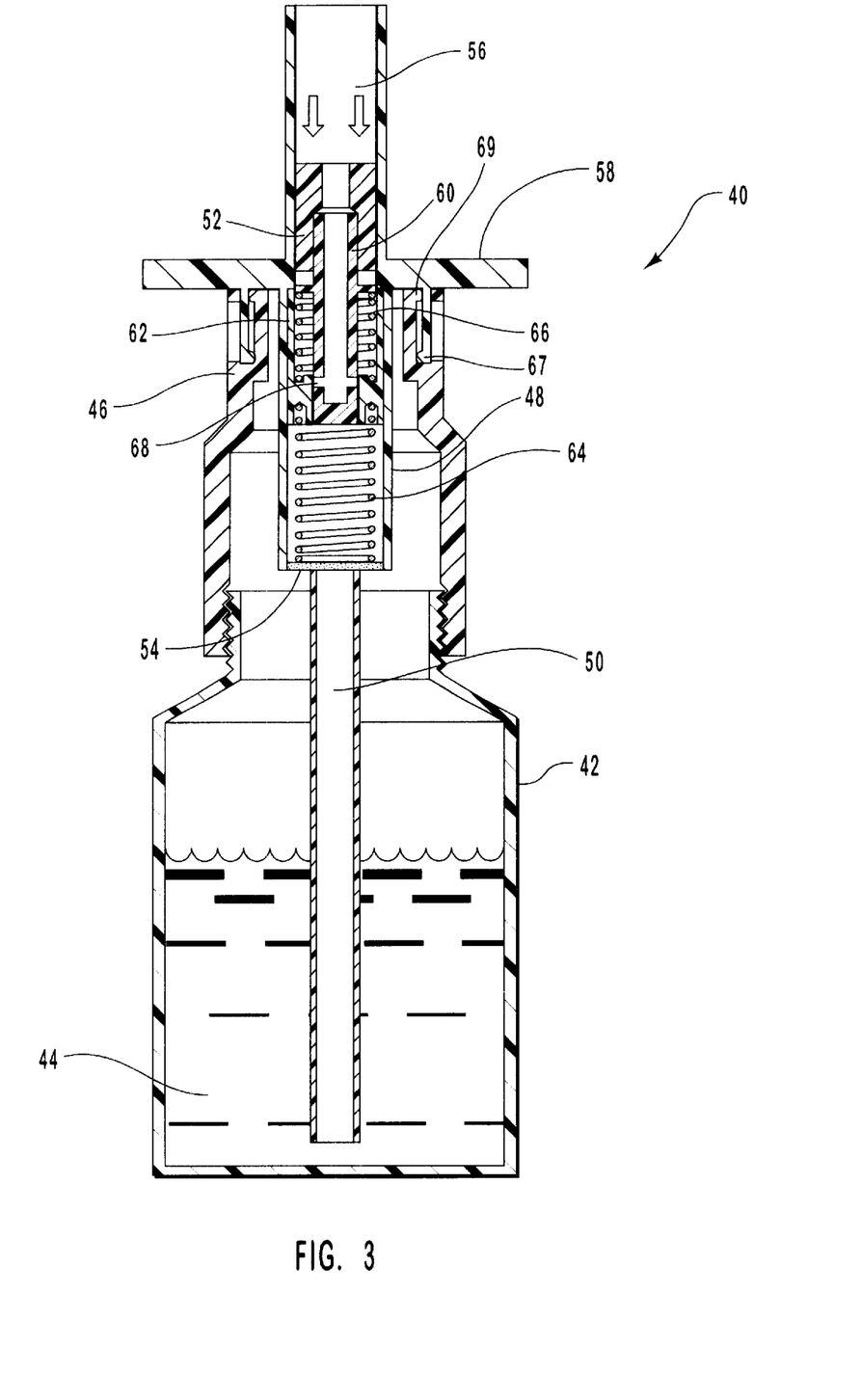
FIGS. 3 and 3A is a cross-sectional view of an exemplary pump sprayer capable of providing metered delivery of a nasal deliverable anesthetizing composition into a patient's nasal cavity.

FIG. 3 alternatively depicts a pump sprayer 40 capable of providing a metered quantity of a liquid composition. The pump sprayer 40 includes a reservoir bottle 42 capable of holding a liquid composition 44 therein, a screw top 46 threadably attached to the bottle 42, a holding chamber 48 nonmovably affixed to the screw top 46, a tube 50 nonmovably affixed to the holding chamber 48, and a pump mechanism 52 slidably attached to the screw top 46 and slidable disposed within the holding chamber 48. A pressure sensitive membrane 54 disposed at the interface between the holding chamber 48 and the tube 50 allows for one-way fluid flow from the tube 50 into the holding chamber 48 as the pump mechanism 52 is pumped.

The pump mechanism 52 includes a nasal delivery tube 56 sized so as delivery the liquid composition 44 into a person's nose, a flange 58 nonmovably affixed to the nasal delivery tube and configured to facilitate pumping of the pump mechanism relative to the bottle 42 and screw top 46, a pump tube 60 nonmovably affixed to the delivery tube 56, and a pump/valve sleeve 62 slidably disposed within the holding chamber 48 and slidably disposed around at least a portion of the outer circumference of the pump tube 60. The pump tube 60 includes one or more circumferential holes 68 which communicate between the outer circumference and the interior of the pump tube 60 but which are initially sealed against the inner wall of the pump/valve sleeve 62 when the pump tube 60 is retracted within the pump/valve sleeve 62.

Figure 3A:
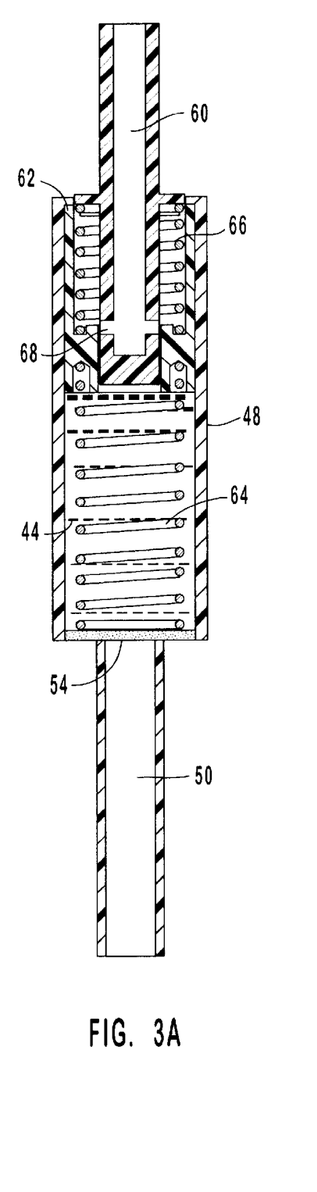

As more particularly seen in FIG. 3A, a pump spring 64 disposed within the holding chamber 48 mechanically interfaces between the holding chamber 48 and the pump/valve sleeve 62 so as to urge the pump/valve sleeve 62 outwardly relative to the holding chamber 48. A valve spring 66 mechanically interfaces between the pump/valve sleeve 62 and the nasal delivery tube 56 so as to urge the nasal delivery tube 56, the pump tube 60 and other associate structures outwardly relative to the pump/valve sleeve 62, thus sealing the circumferential holes of the pump tube 60. While in a resting position, the pump spring 64 and valve spring 66 together urge the entire pump mechanism outwardly relative to the bottle 42 and screw top 46 into an extended position. A detente or stop mechanism 67 associated with the pump mechanism 52 interfaces with a corresponding detente or stop mechanism 69 within the screw top 46 so as to advantageously prevent the pump mechanism 52 from being completely detached from the bottle 42 and screw top 46 (FIG. 3).

Figure 3B:
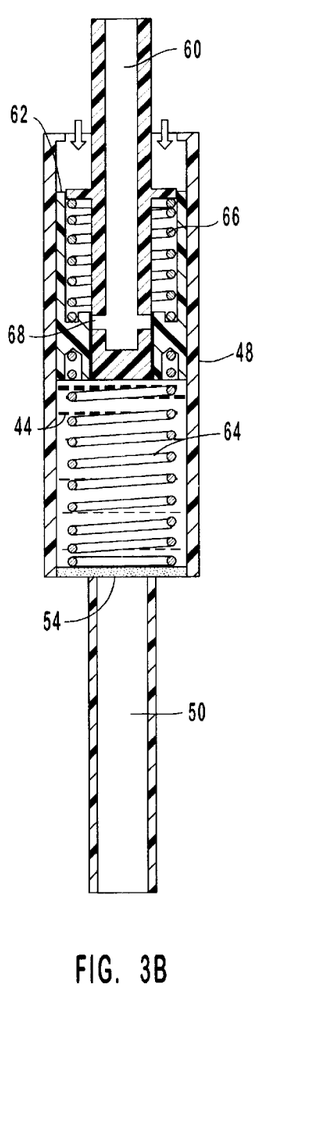
FIGS. 3B and 3C are close-up cross-sectional views of the pump/valve mechanism of the pump sprayer of FIG. 3A depicted in various stages as the pump sprayer is being pumped.
Figure 3C:
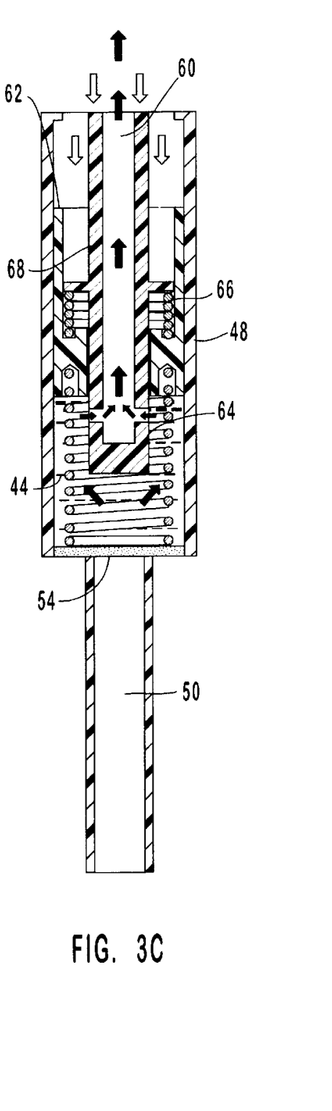

As shown sequentially in FIGS. 3A–3C, upon squeezing the pump mechanism 52 toward the bottle 42, such as by means of a squeezing or clenching action by the user's hands and/or fingers between the flange 58 and bottle 42, the pump/valve sleeve 62 is caused to slide downward through the holding chamber 48 against the force of the pump spring 64 (FIG. 3B). Typically, the valve spring 66 is stronger than the pump spring 64 so that the pump spring 64 is at least partially compressed before the valve spring 66 becomes compressed as a result of the pumping action. As the pump spring 64 is compressed, its force increases until, at some point, its force equals or exceeds the force of the valve spring 66. At this point, further inward pumping of the pump mechanism 52 will compress the valve spring 66, thereby causing the pump tube 60 to slide inwardly relative to the pump/valve sleeve 62. This allows the circumferential holes 68 of the pump tube 60 to become exposed, thus providing fluid communication between the holding chamber 48 and the pump tube 60 as the pump tube 60 slides inwardly relative to the pump/valve sleeve 62 (FIG. 3C). The pumping action causes a metered quantity of the liquid composition 44 from within the holding chamber 48 to be expelled through the circumferential holes 68 and interior of the pump tube 60 and out the nasal delivery tube 56. If the pump sprayer 40 is being used for the first time, it may be necessary to depress and release the pump mechanism 52 multiple times in order to initially fill the holding chamber 48 with the liquid composition 44.

Figure 4A:
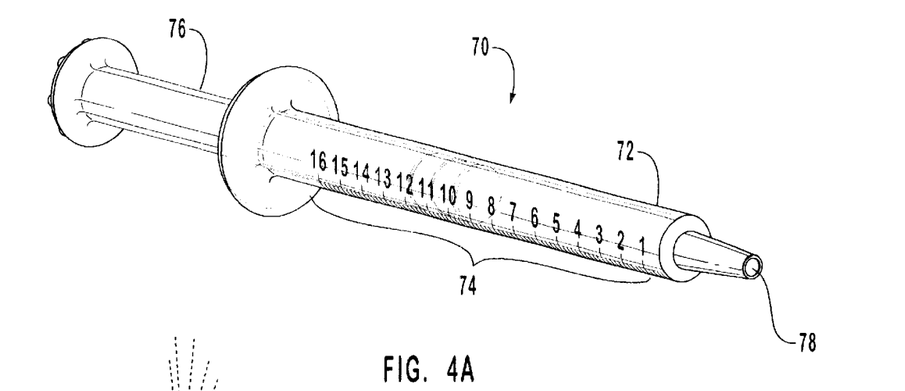
FIG. 4A is side perspective view of an exemplary syringe that may be used to deliver a nasal deliverable anesthetizing composition into a patient's nasal cavity.

FIG. 4A alternatively depicts a syringe 70 capable of providing a measured dose of a liquid or gel into a patient's nasal cavity. In particular, the syringe 70 includes a hollow barrel 72 capable of holding therein a liquid or gel. The barrel 72 includes hash marks 74 corresponding to various dosages of the liquid or gel. A plunger 76 disposed within the barrel 72, upon being depressed by the user, provides pressure that expels a desired quantity of a liquid or gel from an opening 78 at one end of the syringe barrel 72. A removable blocking ring (not shown) may be included on the shaft of the syringe plunger to limit plunger travel such that only a desired quantity of liquid or gel may be expressed at a time. This may be desirable to restrict dosage for children or to allow delivery of the vasoconstrictor portion of the syringe contents and the subsequent delivery of the anesthetic portion of the syringe contents.

An alternative syringe design consists of a nondisposable, sterilizable syringe body that is used in conjunction with anesthetic and/or vasoconstrictor containing single-use cartridges (not shown). The syringe body may be spring-loaded so as to provide a sufficient and consistent force for fluid injection into the nasal cavity. For this embodiment, the clinician would preload a spring device (not shown) such that release of the spring would propel the contents of the cartridge into the patient's nasal cavity.

An alternative method for assuring consistent and sufficient application forces is to incorporate a burstable membrane (not shown) within the anesthetic and vasoconstrictor cartridge design. For this embodiment, the clinician would apply increasing pressure on the syringe plunger, thereby pressurizing the cartridge contents until a critical rupture pressure is reached and the contents are rapidly expelled. A variation of this design allows vasoconstrictor dosing followed by anesthetic dosing from a single disposable syringe (not shown).

Figure 4B:
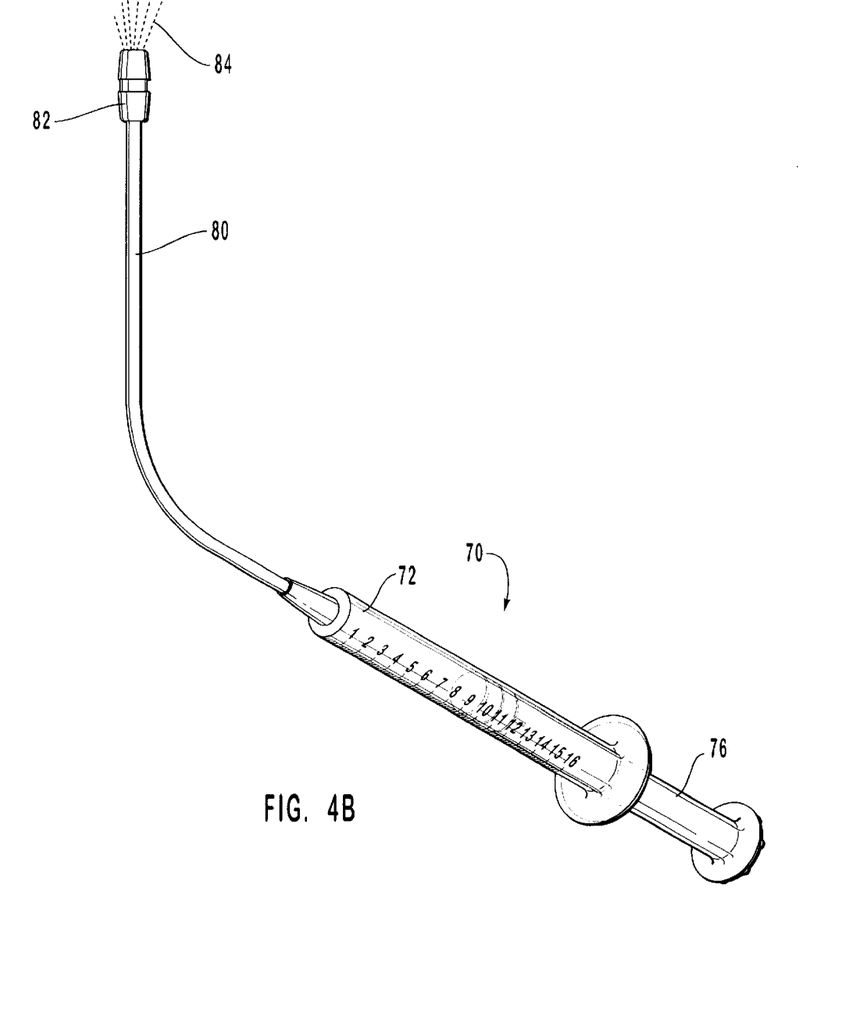
FIG. 4B is a side perspective view of the syringe depicted in FIG. 4A with an extended nasal tube attached thereto for delivering a nasal deliverable anesthetizing composition at a particular location deep within a patient's nasal cavity.

FIG. 4B depicts the syringe 70 of FIG. 4A, to which an extension tube 80 has been attached. The extension tube 80 includes a spray tip 82 capable of providing a fine spray 84 of a liquid or gel held within the syringe barrel 72 upon depressing the plunger 76. This arrangement allows for direct placement of liquid or gel 84 deeper into a patient's nasal cavity. The extension tube 80 may alternatively be attached to any known dispenser in order to provide for deeper placement of liquid or gel within the patient's nasal cavity. The extension tube 80 may alternatively be terminated by an exit port that directs the liquid spray at an angle approximately 90° from the longitudinal axis of the extension tube (FIG. 7).

Figure 5:
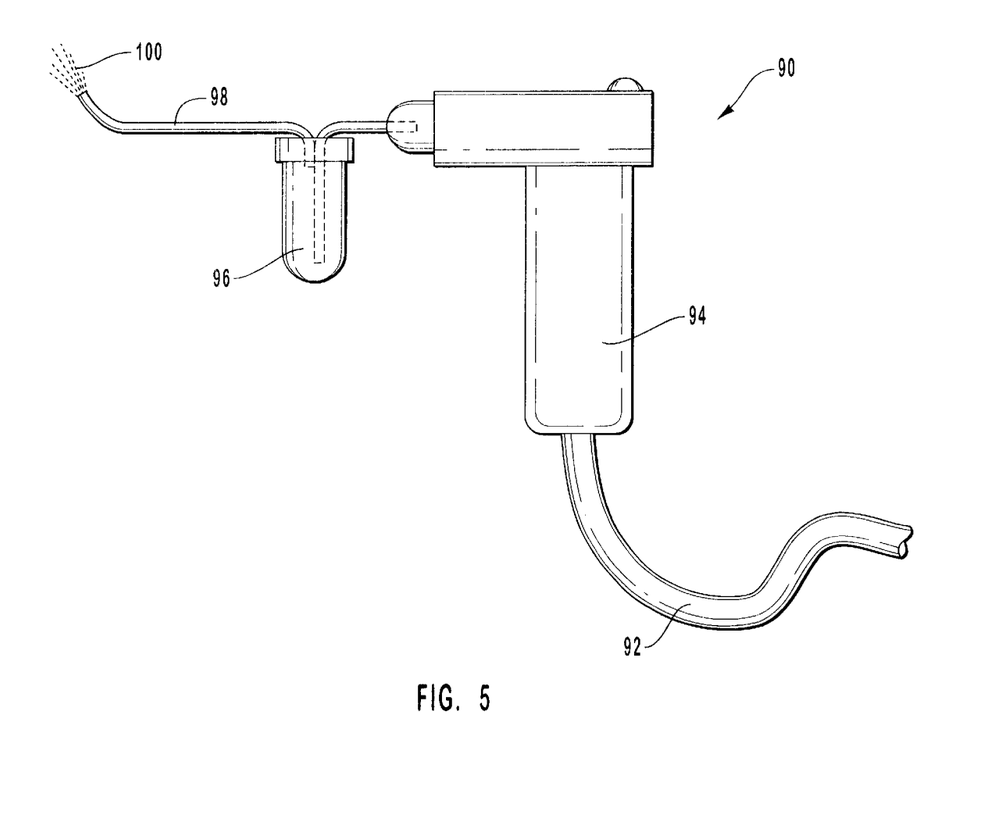
FIG. 5 is a side perspective view of an exemplary pneumatic sprayer capable of providing a volumetrically metered quantity of a nasal deliverable anesthetizing composition deeply into a patient's nasal cavity.

FIG. 5 depicts a pneumatically pressurized sprayer 90, which includes a pressurized hose 92, an actuating handle 94, a reservoir 96, and a nasal insertion tube 98 capable of providing a desired spray pattern 100 of a liquid, gel or powder composition. The sprayer depicted in FIG. 5 may be placed at a variety of depths within the patient's nasal cavity as desired to provide an appropriate spray or application of the anesthetic composition.

Figure 6:
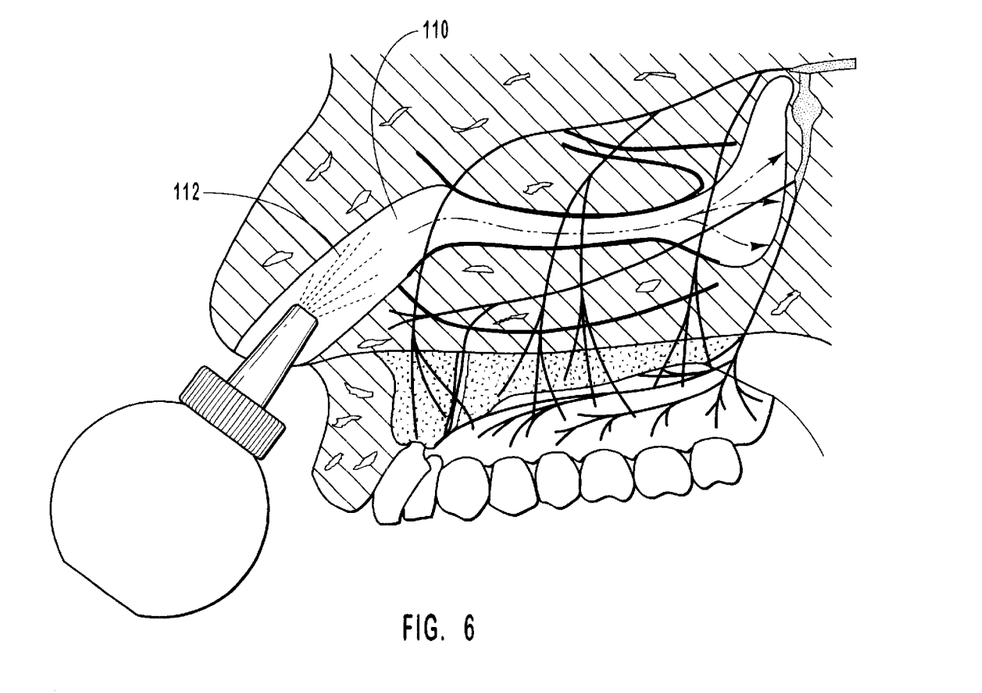
FIG. 6 is a cross-sectional side view of a nasal cavity into which a fine spray of a nasal deliverable anesthetizing composition is introduced just inside the opening of the nostril.

FIG. 6 depicts a nasal cavity 110 into which a liquid or gel composition is delivered in the form of a spray or mist 112. In particular, FIG. 6 depicts a spray bottle, such as the one depicted in FIG. 2, being used to provide an inhalable spray or mist 112, which advantageously becomes atomized and is capable of thereby traveling throughout the nasal cavity 110, including the rear of the nasal cavity 110, for penetration and absorption by nasal tissue, particularly the desired nervous tissues.

Figure 7:
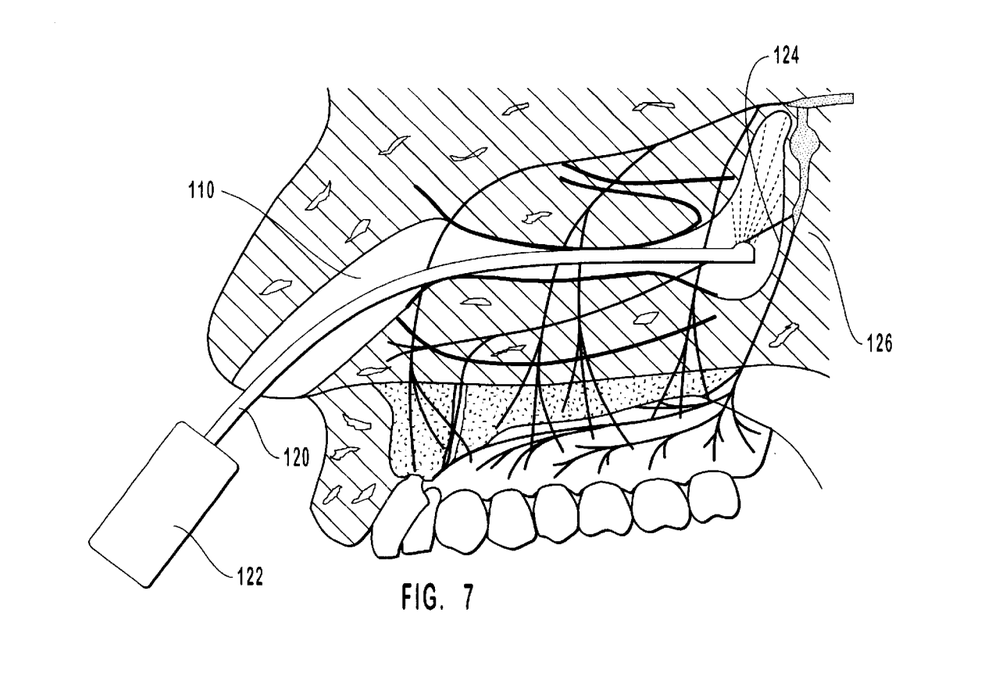
FIG. 7 is a cross-sectional side view of a nasal cavity into which a fine spray of a nasal deliverable anesthetizing composition is introduced deeply inside the nasal cavity by means of an extended tube.

In the alternative, FIG. 7 depicts an extension tube 120 attached to a generic delivery device 122 for focusing a spray 124 of liquid, gel or power at the rear 126 of the nasal cavity 110. The extension tube 120 may be used with any known delivery device. It may be used to deliver liquids, gels and powders to the rear of a patient's nasal cavity.

Figure 8A:
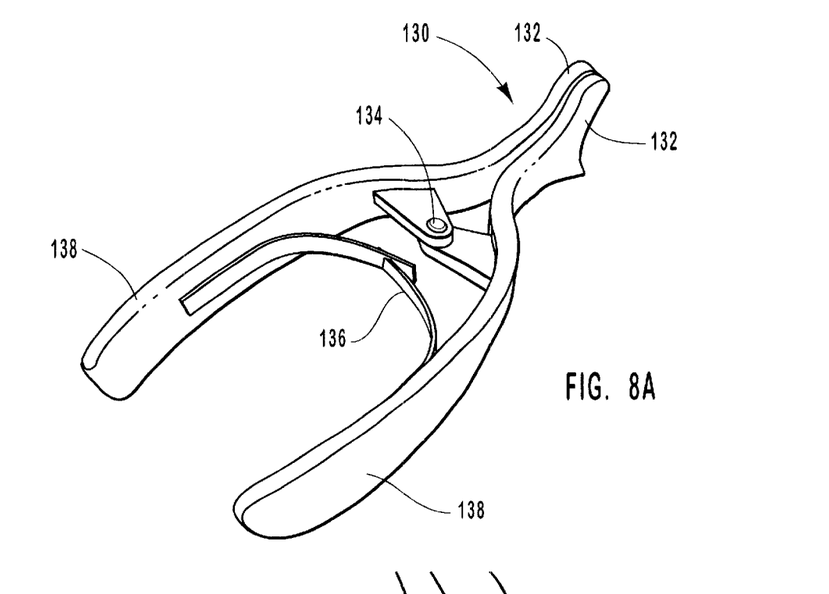
FIG. 8A is a front perspective view of a nasal speculum used to physically dilate a nostril.
Figure 8B:
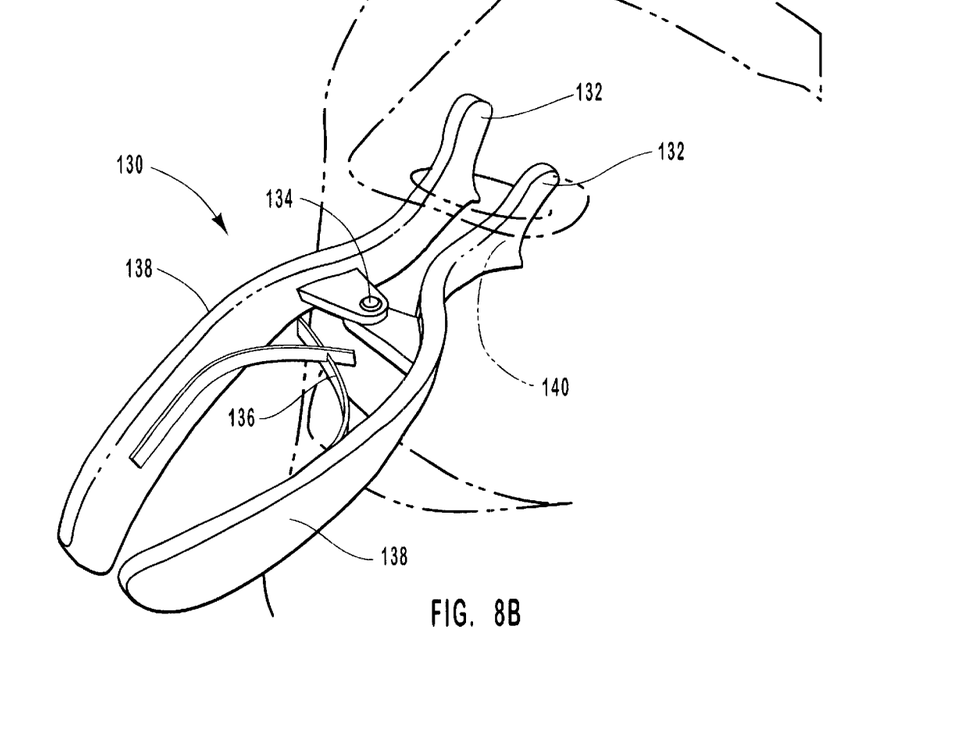
FIG. 8B is front perspective view of the nasal speculum of FIG. 8A being used to physically dilate a nostril.

FIG. 8A illustrates a nasal speculum 130 that may be used to dilate a person's nostril in order to facilitate placement of an extension tube or other invasive delivery device within the person's nostril and nasal cavity. The nasal speculum 130 includes a pair of spreadable tongs 132 connected by a hinge 134, a leaf spring 136 capable of being interlocked so as to maintain the tongs 132 in a spread apart position, and a pair of squeeze bars 138 that may be manipulated so as to spread apart the tongs 132. FIG. 8B shows the nasal speculum 130 being used to dilate a person's nostril 140 preparatory to inserting an extension tube or over delivery device (not shown) into the nostril 140.

B. Kits.

The nasal deliverable anesthetic compositions according to the present invention may advantageously be provided in the form of a kit for added convenience. The kit may include, for example, one or more delivery devices for delivering an appropriate liquid, gel or powder composition. In those cases where all of the active agents are contained within a single composition, it may be possible to provide a single delivery device. In other cases, where the components of the nasal deliverable anesthetic composition are provided in two or more separate liquids or gels, they may be provided within two or more delivery devices.

For example, in order to maximize the initial effect of the vasoconstrictor so as to thereby maximize the rate of penetration and extent of absorption of the anesthetic by the nasal tissue, it may be advantageous to provide a vasoconstrictor in a first delivery device separate from a second delivery device containing the anesthetic. The same may be true for other active ingredients, such as an antihistamine spray to inhibit running or nasal drip.

Other components that may be included within a kit include, but are not limited to, one or more nasal extension tubes for deeper nasal delivery of one or more of the compositions, a topical anesthetic for the gingiva, an antihistamine or other substance for inhibiting nasal drip, and a nasal speculum for dilating the patient's nostril. The topical anesthetic may be applied using any means known in the art for applying a topical anesthetic, including, but not limited to, the aforementioned delivery devices, swabs, brushes, sponges, pads, patches, and the like.

In order to prevent infection from one patient to another, the delivery devices will preferably include a single dose of the composition held therein. Nevertheless, it is certainly within the scope of the invention to provide multiple doses, particularly in the case where it may be necessary to increase the initial dose in order to provide further numbing and anesthetizing of the relevant tissue. Multiple dose delivery devices may be equipped with removable and replaceable nozzle tips or other disposable components to prevent cross contamination from one patient to another.

IV. Methods for Anesthetizing Teeth and Surrounding Tissue

As set forth above, the inventive nasal deliverable anesthetic compositions are delivered to the patient through the nasal cavity. This is done by applying the anesthetic composition to the lateral wall or membrane of the nasal cavity, where it can be absorbed into the nasal tissue, including nerves located within the nasal tissue. In the case where a delivery device having an extension tube is used, good results have been obtained by inserting approximately 15 mm of the tube into the patient's nasal cavity through the nostril. A nasal speculum may advantageously be used to assist in dilating the patient's nostril preparatory to inserting the extension tube so as to facilitate placement of the tube in a desired location within the patient's nasal cavity.

As discussed above with respect to FIG. 1, the nasal cavity includes a number of nerves that are responsible for transmitting pain and pressure impulses from the maxillary arch and palate to the brain. Most of these nerves collect at and below the maxillary nerve. Due to the location of the various nerves that collect at or below the maxillary nerve it may be possible to provide various degrees of anesthesia. Control of dosage volume, through control of the number of substance dispensing, can be utilized to determine the anatomical structures to be anesthetized. Minimal dosage volumes tend to yield anesthesia to at least a portion of the maxillary dentition, while greater anesthetic dosages yield anesthesia to the entire maxillary arch.

For example, it has been found that the front teeth are typically anesthetized first, which seems to indicate that the anterior superior alveolar nerve is closer to the membrane surface than the middle and posterior superior alveolar nerves. Thus, where it is desired to only anesthetize the front teeth, a smaller dosage of the anesthetic composition may be applied in order to limit the depth of absorption through the nerve bundle. Applying progressively greater quantities of the anesthetic composition successively provides anesthesia to the other two regions of the teeth as more of the anesthetic is able to penetrate deeper below the membrane surface and be absorbed by nerves located more deeply below the surface. In this way, some or all of the teeth can be anesthetized.

In addition, the alveolar nerves, maxillary nerve and pterygopalatine ganglion are specific to the left and right sides of a person's mouth. Therefore, it is possible to anesthetize just the left or right side of a patient's maxillary dental arch by delivering the anesthetizing composition in either the left or right nostrils. It is possible in this way to focus the anesthetizing of the patient's teeth in order to avoid anesthetizing teeth not subject to invasive dental work.

The hard and soft palates are likewise anesthetized more slowly than the teeth, which appears to indicate that the greater and lesser palatine nerves are located deeper below the membrane surface than the anterior, middle and posterior superior alveolar nerves. Thus, it may be possible to avoid anesthetizing the hard and soft palates when they are not subject to an invasive and painful procedure. Anesthetizing the greater palatine nerve is responsible for the hard palate anesthesia of a patient in the case of more radical periodontal surgery. In addition, the lesser palatine nerve, which controls the soft palate, may inhibit or prevent the gag reflex altogether, thereby further assisting the dentist in carrying out a desired dental procedure.

As stated above, it may be advantageous to first apply the vasoconstrictor in order to shrink the tissue of the nasal membrane. This assists in promoting subsequent absorption of the anesthetic by the nasal tissue. Because the shrinking of the nasal membrane may take a few minutes, it may be preferable to first apply the vasoconstrictor prior to applying the anesthetic. In this way, less of the anesthetic will tend to be wasted by either being more diffusely absorbed rather than in the targeted location. In short, applying the vasoconstrictor first before applying the anesthetic may facilitate more efficient and rapid absorption of the anesthetic at the targeted location.

In addition, the vasoconstrictor may be useful in slowing down blood circulation locally within the nasal tissue. This, in turn, is believed to inhibit systemic migration of the anesthetic into outlying tissue or even other areas of the circulatory system. Limiting migration of the anesthetic would be expected to focus the initial anesthetizing properties in the desired location and also maintain the desired level of anesthesia by better maintaining the concentration of the anesthetic in the targeted region. Inhibiting systemic migration of the anesthetic also tends to slow down the rate of destruction of the anesthetic by bodily enzymes.

Finally, other optional agents, such as an antihistamine or other anti-nasal drip agents may be applied before, during, or after the application of the aforementioned vasoconstrictor and anesthetic.

In a preferred embodiment, one or more of the active compositions are applied by means of an extension tube that is inserted deep into a patient's nasal cavity in order to focus application of the anesthetic and/or vasoconstrictor in a desired location. In order to facilitate insertion of the tube, a nasal speculum may be used to dilate the nostril into which the tube is inserted. Of course, as the application of the nasal deliverable anesthetic composition becomes more elaborate and intrusive, some of the benefit of the present invention may be compromised, particularly with respect to patient comfort, not to mention fear and anxiety of the patient.

The anesthetizing properties of the nasal deliverable anesthetizing compositions of the present invention are generally limited to the maxillary dentition and surrounding tissue, including the hard and soft palates. The facial gingiva generally retain most or all of their normal sensation even after application of the nasal deliverable anesthetizing compositions according to the present invention. This may be desirable in the case where only the teeth are being worked on, thereby minimizing patient discomfort and numbness where it is not needed. On the other hand, in the case of more intrusive periodontal procedures in which the gingiva will be subject to cutting, or other trauma, it may be advantageous to apply a topical anesthetic to the gingiva.

V. Examples of Preferred Compositions

In order to more clearly illustrate the parameters of the inventive anesthetic compositions within the scope of the present invention, the following examples are presented. The following examples are intended to be exemplary and should not be viewed as limiting to the scope of the invention. Examples that are presented in past tense are actual compositions that were prepared whereas examples written in present tense are hypothetical in nature. Even though one or more examples may be hypothetical, they are based on actual mix designs and have been modified in order to more fully define what the inventor regards as his invention.

EXAMPLE 1

A nasal deliverable anesthetizing composition within the scope of the invention was prepared by combining the following ingredients in the following proportions, expressed in terms of weight percent:

| Tetracaine HCl | 2% |
| --- | --- |
| Oxymetazoline HCl | 0.05% |
| Aqueous Saline Solution (0.9%) | 97.95% |

The tetracaine portion included an associated chlorobutanol preservative. The aqueous solution included sodium chloride in water. The nasal deliverable anesthetizing composition, when applied to a patient's nasal cavity, was found to provide profound anesthesia of part of all of the maxillary dental arch depending on how much of the composition was applied. The Oxymetazoline HCl enhanced the absorption of the tetracaine compared to a tetracaine composition that was applied to nasal tissue that was not treated with a vasoconstrictor.

EXAMPLE 2

A nasal deliverable anesthetizing composition within the scope of the invention was prepared by combining the following ingredients in the following proportions, expressed in terms of weight percent:

| Lidocaine HCl | 4% |
| --- | --- |
| Oxymetazoline HCl | 0.05% |
| Aqueous Saline Solution (0.9%) | 95.95% |

The lidocaine portion included an associated preservative. The aqueous solution included sodium chloride in water. The nasal deliverable anesthetizing composition, when applied to a patient's nasal cavity, was found to provide profound anesthesia of part of all of the maxillary dental arch depending on how much of the composition was applied. The oxymetazoline HCl enhanced the anesthetic effect of the lidocaine compared to a lidocaine composition that was applied to nasal tissue that was not treated with a vasoconstrictor.

EXAMPLE 3

A nasal deliverable anesthetizing composition within the scope of the invention was prepared by combining the following ingredients in the following proportions, expressed in terms of weight percent:

| Benzocaine HCl | 15% |
| --- | --- |
| Oxymetazoline HCl | 0.05% |
| Aqueous Saline Solution (0.9%) | 84.95% |

The benzocaine portion included an associated preservative. The aqueous solution included sodium chloride in water. The nasal deliverable anesthetizing composition, when applied to a patient's nasal cavity, was found to provide profound anesthesia of part of all of the maxillary dental arch depending on how much of the composition was applied. The oxymetazoline HCl enhanced the absorption of the benzocaine compared to a benzocaine composition that was applied to nasal tissue that was not treated with a vasoconstrictor.

EXAMPLE 4

A nasal deliverable anesthetizing composition within the scope of the invention was prepared by combining the following ingredients in the following proportions, expressed in terms of weight percent:

| Cocaine HCl | 4% |
| --- | --- |
| Aqueous Saline Solution (0.9%) | 96% |

The cocaine hydrochloride portion included an associated preservative. The aqueous solution included sodium chloride in water. The nasal deliverable anesthetizing composition, when applied to a patient's nasal cavity, was found to provide profound anesthesia of part of all of the maxillary dental arch depending on how much of the composition was applied.

EXAMPLE 5

Any of the foregoing compositions is altered by replacing the anesthetic with 0.5% of dyclonine hydrochloride, expressed in terms of weight percent.

EXAMPLE 6

Any of the foregoing compositions is altered by replacing the anesthetic with 4% of dyclonine hydrochloride, expressed in terms of weight percent.

EXAMPLE 7

Any of the foregoing compositions is altered by replacing the vasoconstrictor with 0.0004% of phenylephrine HCl, expressed in terms of weight percent.

EXAMPLE 8

Any of the foregoing compositions is altered by replacing the vasoconstrictor with 0.00005% of levodexoxyephedrine, expressed in terms of weight percent.

EXAMPLE 9

Any of the foregoing compositions is altered by replacing the vasoconstrictor with 0.00001% of norepinephrine, expressed in terms of weight percent.

EXAMPLE 10

Any of the foregoing compositions is altered by replacing the vasoconstrictor with 0.00001% of epinephrine, expressed in terms of weight percent.

EXAMPLE 11

Any of the foregoing compositions can be altered by dividing the anesthetic and vasoconstrictor into two separate compositions. The two separate compositions have the same concentration of the respective active agents, with the balance comprising the aqueous saline solution (0.9%).

EXAMPLE 12

Any of the foregoing compositions is altered by adding a topical gingival anesthetic such as, but not limited to, 2% or 4% viscous lidocaine, 20% benzocaine, 0.5% or 1.0% dyclonine HCl, 2% or 4% tetracaine, or Cetacaine®.

EXAMPLE 13

Any of the foregoing compositions is altered by adding a composition capable of inhibiting nasal drainage such as, but not limited to, atropine or azelastine HCl.

EXAMPLE 14

Any of the foregoing compositions may be provided in a one or multi-part (e.g., two-part) kit, including a delivery device capable of delivering a desired quantity of the one or multi-part compositions. The kit may optionally include a topical anesthetic in a separate delivery device for numbing gingival tissue, such as a viscous gel containing 20% benzocaine HCl.

VI. Summary

In conclusion, the invention provides improved methods and systems for delivering a local anesthetic in connection with painful dental procedures, which is less painful to administer compared to conventional needle delivered anesthetics.

The invention additionally provides methods and systems for delivering a local anesthetic in connection with painful dental procedures which eliminate the use of needle delivered anesthetics altogether, at least with respect to a portion of a patient's teeth, particularly at least a portion of the patient's maxillary dental arch, which is the most painful to anesthetize using a needle.

The invention yet provides methods and systems for painlessly delivering a local anesthetic without the use of a needle and which also provide complete and total anesthetization of at least a portion of a patient's teeth, particularly at least a portion of the patient's upper dental arch, which is the most painful to anesthetize using a needle.

The invention further provides methods and systems for painlessly anesthetizing a patient's teeth without the use of a needle, which further allows for the painless anesthetization of surrounding gingival tissues.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for selectively targeting and anesthetizing at least a portion of a patient's maxillary dental arch comprising:
   (a) providing a nasally deliverable anesthetizing composition which includes a pharmaceutically effective amount of an anesthetizing agent; and
   (b) selectively delivering a quantity of the anesthetizing composition into the rear of the patient's nasal cavity in order for at least a portion of the anesthetizing composition to be absorbed by nasal tissue located at the rear of the nasal cavity in the vicinity of at least one nerve responsible for transmitting pain impulses from at least a portion of the maxillary dental arch to the patient's brain in order to thereby selectively and remotely anesthetize at least that portion of the patient's maxillary dental arch.

2. A method as defined in claim 1, wherein the anesthetizing composition is applied and absorbed in a manner so as to selectively and remotely anesthetize at least one tooth of at least one hemisphere of the maxillary dental arch.

3. A method as defined in claim 1, wherein the anesthetizing composition is applied and absorbed in a manner so as to selectively anesthetize at least one of the anterior superior alveolar nerve, middle superior alveolar nerve, posterior alveolar nerve, or preceding nerves in order to selectively and remotely anesthetize at least one tooth of at least one hemisphere of the maxillary dental arch.

4. A method as defined in claim 1, wherein the anesthetizing composition is applied and absorbed in a manner so as to selectively anesthetize at least one of the greater palatine nerve or preceding nerves in order to selectively and remotely anesthetize at least a portion of the hard palate.

5. A method as defined in claim 1, wherein the anesthetizing composition is applied and absorbed in a manner so as to selectively anesthetize at least one of the lesser palatine nerve or preceding nerves in order to selectively and remotely anesthetize at least a portion of the soft palate.

6. A method as defined in claim 1, wherein the anesthetizing agent comprises at least one of tetracaine, lidocaine, benzocaine, dyclonine, pramoxine, dibucaine, butacaine, cocaine, salts of the foregoing, or analogues of the foregoing.

7. A method as defined in claim 1, further comprising administering a vasoconstrictor into the patient's nasal cavity in order to promote penetration and absorption of the anesthetizing agent by nasal tissue located at the rear of the nasal cavity.

8. A method as defined in claim 7, wherein the vasoconstrictor is administered in a manner so as to inhibit migration of the anesthetizing agent away from the at least one nerve.

9. A method as defined in claim 7, wherein the vasoconstrictor comprises at least one of oxymetazoline hydrochloride, phenylephrine hydrochloride, naphazoline hydrochloride, propylhexadrine, levodesoxyephedrine, or analogues of the foregoing.

10. A method as defined in claim 7, wherein at least a portion of the vasoconstrictor is included within the anesthetizing composition and administered together with the anesthetizing agent.

11. A method as defined in claim 7, wherein at least a portion of the vasoconstrictor is administered separately from the anesthetizing agent.

12. A method as defined in claim 1, wherein the anesthetizing composition includes one or more inert ingredients for modification of at least one of substance wetting, control of mixture viscosity, control of mixture pH, or control of mixture dilution.

13. A method as defined in claim 1, wherein the anesthetizing composition is at least one of a liquid, solution suspension, gel, or powder.

14. A method as defined in claim 1, wherein the anesthetizing composition is delivered into the patient's nasal cavity by means of a delivery device configured so as to preferentially deliver a desired dosage of the anesthetizing composition to the rear of the nasal cavity.

15. A method as defined in claim 1, further comprising topically applying an anesthetic composition to gingival tissue in order to anesthetize the gingival tissue.

16. A method as defined in claim 1, further comprising administering a nasal drip inhibiting agent in order to inhibit dripping of fluid from the patient's nasal cavity.

17. A method as defined in claim 1, wherein the anesthetizing composition further includes water prior to delivery of the anesthetizing composition to the patient's nasal cavity.

18. A method as defined in claim 1, further comprising performing at least one procedure involving at least a portion of the patient's maxillary dental arch that would otherwise result in pain or discomfort absent anesthetization of at least a portion of the patient's maxillary dental arch.

19. A method for selectively targeting and anesthetizing at least a portion of a patient's maxillary dental arch comprising:
(a) providing an anesthetizing composition which includes a pharmaceutically effective amount of an anesthetizing agent;
(b) selectively delivering a quantity of the anesthetizing composition into the rear of the patient's nasal cavity in order for at least a portion of the anesthetizing composition to penetrate and be absorbed by nasal tissue located at the rear of the nasal cavity in the vicinity of at least one nerve responsible for transmitting pain impulses from at least a portion of the maxillary dental arch to the patient's brain in order to thereby selectively and remotely anesthetize at least a portion of the patient's maxillary dental arch;
(c) providing a vasoconstrictor; and
(d) selectively introducing a desired quantity of the vasoconstrictor into the patient's nasal cavity in order to promote absorption of the anesthetizing composition by the nasal tissue located at the rear of the nasal cavity and inhibit migration of the anesthetizing composition away from the vicinity of the at least one nerve responsible for transmitting pain impulses from at least one tooth of the maxillary dental arch to the patient's brain.

20. A method as defined in claim 19, wherein at least a portion of the vasoconstrictor is introduced into the patient's nasal cavity prior to introducing the anesthetizing composition.

21. A method as defined in claim 19, wherein at least a portion of the vasoconstrictor is introduced into the patient's nasal cavity at the same time as the anesthetizing composition.

22. A method as defined in claim 19, wherein at least a portion of the vasoconstrictor is introduced into the patient's nasal cavity subsequent to introducing the anesthetizing composition.

23. A method as defined in claim 19, wherein the anesthetizing composition further includes water prior to delivery of the anesthetizing composition to the patient's nasal cavity.

24. A method as defined in claim 19, further comprising performing at least one procedure involving at least a portion of the patient's maxillary dental arch that would otherwise result in pain or discomfort absent anesthetization of at least a portion of the patient's maxillary dental arch.

25. A method for selectively targeting and anesthetizing at least a portion of a patient's maxillary dental arch comprising:
(a) providing a nasally deliverable aqueous anesthetizing composition which includes a pharmaceutically effective amount of an anesthetizing agent;
(b) selectively delivering a quantity of the aqueous anesthetizing composition into the rear of the patient's nasal cavity in order for at least a portion of the anesthetizing composition to be absorbed by nasal tissue located at the rear of the nasal cavity in the vicinity of at least one nerve responsible for transmitting pain impulses from at least a portion of the maxillary dental arch to the patient's brain in order to thereby selectively and remotely anesthetize at least that portion of the patient's maxillary dental arch; and
(c) performing at least one procedure involving at least a portion of the patient's maxillary dental arch that would otherwise result in pain or discomfort absent anesthetization of at least a portion of the patient's maxillary dental arch.

26. A method as defined in claim 25, wherein the anesthetizing composition is applied and absorbed in a manner so as to anesthetize at least one of the anterior superior alveolar nerve, middle superior alveolar nerve, posterior superior alveolar nerve, or preceding nerves in order to anesthetize at least one tooth of at least one hemisphere of the maxillary dental arch.

27. A method as defined in claim 25, wherein the anesthetizing composition is applied and absorbed in a manner so as to selectively anesthetize at least one of the greater palatine nerve, the lesser palatine nerve, or preceding nerves in order to anesthetize at least a portion of the hard palate, the soft palate, or both.

28. A method as defined in claim 25, wherein the anesthetizing agent comprises at least one of tetracaine, lidocaine, benzocaine, dyclonine, pramoxine, dibucaine, butacaine, cocaine, salts of the foregoing, or analogues of the foregoing.

29. A method as defined in claim 25, further comprising administering a vasoconstrictor into the patient's nasal cavity in order to promote penetration and absorption of the anesthetizing agent by nasal tissue located at the rear of the nasal cavity.

30. A method as defined in claim 29, wherein at least a portion of the vasoconstrictor is included within the anesthetizing composition and administered together with the anesthetizing agent.

31. A method as defined in claim 25, wherein the anesthetizing composition is delivered into the patient's nasal cavity by means of a delivery device configured so as to preferentially deliver a desired dosage of the anesthetizing composition to the rear of the nasal cavity.

32. A method as defined in claim 25, wherein the procedure involving at least a portion of the patient's maxillary dental arch comprises at least one of drilling one or more cavities, a root canal procedure, pulling one or more teeth, crown work, or bridge work.

* * * * *